(12) United States Patent
Schiemann et al.

(10) Patent No.: US 7,008,955 B2
(45) Date of Patent: Mar. 7, 2006

(54) (2-AZABICYCLO[2.2.1]HEPT-7YL) METHANOL DERIVATIVES AS NICOTINIC ACETYLCHOLINE RECEPTOR AGONISTS

(75) Inventors: Kai Schiemann, Darmstadt (DE); Joachim Leibrock, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 344 days.

(21) Appl. No.: 10/380,064

(22) PCT Filed: Sep. 11, 2001

(86) PCT No.: PCT/EP01/10491

§ 371 (c)(1), (2), (4) Date: Jul. 9, 2003

(87) PCT Pub. No.: WO02/22578

PCT Pub. Date: Mar. 21, 2002

(65) Prior Publication Data

US 2004/0039045 A1 Feb. 26, 2004

(30) Foreign Application Priority Data

Sep. 12, 2000 (DE) ................ 100 44 905

(51) Int. Cl.
*A61K 31/44* (2006.01)
*A61K 31/435* (2006.01)
*C07D 211/06* (2006.01)

(52) U.S. Cl. ............... 514/357; 546/329; 546/334; 514/277

(58) Field of Classification Search ............... 546/329, 546/334; 514/277, 357
See application file for complete search history.

(56) References Cited

U.S. PATENT DOCUMENTS 5,817,679 A 10/1998 Shen et al.
6,117,889 A * 9/2000 Shen et al. ............... 514/339

FOREIGN PATENT DOCUMENTS

EP 0978280 2/2000
WO WO 9205172 4/1992
WO WO 0023424 4/2000

* cited by examiner

*Primary Examiner*—Golam M. M. Shameem
(74) *Attorney, Agent, or Firm*—Millen, White, Zelano & Branigan, P.C.

(57) ABSTRACT

The present invention relates to substances of the general formula (I)

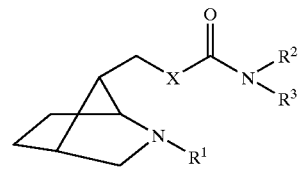

in which
X is selected from the group consisting of NH, $NR^4$, O and S,
$R^1$ is selected from the group consisting of hydrogen, linear and branched, substituted and unsubstituted $C_1$–$C_{10}$-alkyl groups, substituted and unsubstituted $C_5$–$C_{10}$-aryl groups, substituted and unsubstituted $C_4$–$C_{10}$-heteroaryl groups, acyl groups, thioacyl groups, carbonylcarboxy groups, N-organyl-substituted carbamoyl groups and organosulfonyl groups,
$R^2$, $R^3$ are selected, independently of one another, from the group consisting of $C_1$–$C_{10}$-alkyl groups, $C_5$–$C_{12}$-aryl groups and $C_4$–$C_{12}$-heteroaryl groups, these groups being unsubstituted or having one or more substituents which are selected, independently of one another, from the group consisting of halogens, alkoxy groups, aryloxy groups, nitro groups, $C_1$–$C_5$-alkoxycarbonyl groups, optionally fluorine-substituted alkyl or acyl groups and cyano groups,
$R^4$ is selected from the group consisting of hydrogen, linear and branched, substituted and unsubstituted $C_1$–$C_{10}$-alkyl groups, substituted and unsubstituted $C_5$–$C_{10}$-aryl groups, substituted and unsubstituted $C_4$–$C_{10}$-heteroaryl groups, aryl groups, thioacryl group, carbonylcarboxy groups, N-organyl-substituted carbamoyl groups and organosulfonyl groups,
or a physiologically acceptable salt thereof.

6 Claims, No Drawings

(2-AZABICYCLO[2.2.1]HEPT-7YL) METHANOL DERIVATIVES AS NICOTINIC ACETYLCHOLINE RECEPTOR AGONISTS

The present invention relates to substances which can be employed for treating diseases in which stimulation of the nicotinic acetylcholine receptors leads to an improvement in the pathological state. The substances of the invention comprise an optionally substituted (2-azabicyclo[2.2.1] hept-7-yl-methyl) unit which is connected to a carbamate, thiocarbamate or urea unit.

Some members of the well-characterized class of acetylcholine receptors are thought to be responsible for certain pathological states of the central nervous system. Known active substances able to interact with the class of acetylcholine receptors are, for example, pilocarpine, nicotine, lobeline and epibatidine.

However, there is still a need for compounds which can be employed for treating pathological states caused by a dysfunction of nicotinic actylchloline receptors The object of the present invention is to provide compounds with which it is possible to treat these pathological states. This object is achieved by substances of the general formula (I)

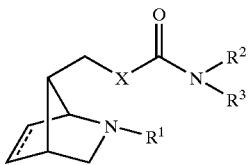

I in which the broken line represents a double bond which is optionally present, X is selected from the group consisting of NH, NR$^4$, O and S, R$^1$ is selected from the group consisting of hydrogen, linear and branched, substituted and unsubstituted C$_1$–C$_{10}$-alkyl groups, substituted and unsubstituted C$_5$–C$_{10}$-aryl groups, substituted and unsubstituted C$_4$–C$_{10}$-heteroaryl groups, acyl groups, thioacyl groups, carbonylcarboxy groups, N-organyl-substituted carbamoyl groups and organosulfonyl groups, R$^2$, R$^3$ and R$^4$ are selected, independently of one another, from the group consisting of C$_1$–C$_{10}$-alkyl groups, C$_5$–C$_{12}$-aryl groups and C$_4$–C$_{12}$-heteroaryl groups, these groups being unsubstituted or having one or more substituents which are selected, independently of one another, from the group consisting of halogens, alkoxy groups, aryloxy groups, nitro groups, C$_1$–C$_5$-alkoxycarbonyl groups, optionally fluorine-substituted alkyl or acyl groups and cyano groups.

It has been found that the substances of the formula (I) are employed specifically for the treatment of diseases in which stimulation of the nicotinic acetylcholine receptors leads to an improvement in the pathological state. Examples are known to the skilled person and comprise schizophrenia, dementia, including in this connection in particular Alzheimer's disease, neurodegenerative diseases, Parkinson's disease and Tourette's syndrome. The substances likewise have neuroprotective activity, which should make use possible for stroke or intoxications.

It is preferred in one embodiment of the present invention when X in the substances of formula (I) is NH, NR$^4$ or O, in particular O, R$^1$ is selected from the group consisting of hydrogen, linear and branched C$_1$–C$_5$-alkyl groups which are unsubstituted or may have as substituents one or more halogen atoms, optionally alkyl-substituted C$_6$–C$_{10}$-aryl groups and/ or C$_1$–C$_5$-alkoxycarbonyl groups, or C$_6$–C$_{12}$-aryl groups and C$_5$–C$_{10}$-heteroaryl groups which may be unsubstituted or have as substituents in each case one or more halogen atoms and/or alkyl groups, or aliphatic C$_1$–C$_5$-acyl and thioacyl groups, aromatic C$_6$–C$_9$-aroyl and thioaroyl groups, carbamoyl groups of the type R$^5$—N(H)—C(O)— and sulfonyl groups of the type R$^5$—SO$_2$—, R$^2$, R$^3$ and R$^4$ are selected, independently of one another, from the group consisting of C$_1$–C$_4$-alkyl groups, the C$_5$–C$_9$-aryl groups and C$_5$–C$_8$-heteroaryl groups which are unsubstituted or have one or more substituents which are selected from the group consisting of C$_1$–C$_4$-alkoxy groups, C$_6$–C$_9$-aryloxy groups, nitro groups, C$_1$–C$_2$-alkoxycarbonyl groups, cyano groups, fluoride, chloride, fluoromethyl groups and acetyl groups.

R$^5$ is selected from the group consisting of C$_1$–C$_3$-alkyl groups, C$_1$–C$_3$-fluoroalkyl groups and phenyl groups which can be unsubstituted or substituted by one or more methyl or trifluoromethyl groups.

In a further embodiment of the present invention it is preferred for the compounds of the formula (I) to have no double bond.

The compounds of the formula (I) are generally prepared by methods known per se, as described in the literature (for example J. March, Advanced Organic Chemistry, 3$^{rd}$ edition, John Wiley & Sons, New York or Houben-Weyl, Methoden der Organischen Chemie [Methods of Organic Chemistry], Georg-Thieme-Verlag, Stuttgart), in particular under reaction conditions known and suitable for said reactions. It is moreover possible to have recourse to variants which are known per se and which are not mentioned in detail hereinafter.

According to the present invention, the substances of the formula (I) are preferably prepared by reacting a substance of the formula (II) which is derived from the formula (I) by replacing a group R$^1$ with a hydrogen atom with a cation R$^{1+}$ which is derived from the group R$^1$ and has a suitable counterion. This is depicted in the following equation (1):

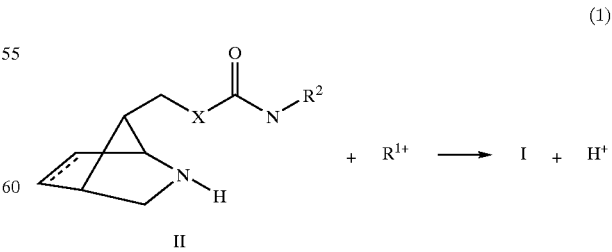

(1)

In equation (1), the substituents R$^1$ and R$^2$ have the meaning indicated for formula (I). The compounds of the formula (II) are prepared from the compounds of the for mula (III) in which A is a suitable protective group for the amino function.

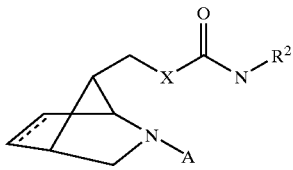

III

A benzyl group is preferably used as protective group. The substances of the invention can be prepared from these compounds (III) by elimination of the protective group, which preferably takes place by hydrogenation, for example using palladium on activated carbon.

The substances of the formula (III) in turn can be obtained from compounds corresponding to formula (IV), specifically by reaction with the appropriate isocyanate $R^2NCO$ having the required radical $R^2$.

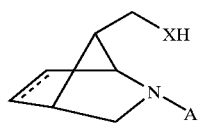

IV

The compounds (IV) are known in the case where X=O, see, for example, WO 92/05172 and literature cited therein. The compounds (IV), in which X is S can be prepared from the corresponding compounds (IV) with X=O by processes known from the literature.

In the case of the compounds (IV) with X=NH or $NR^4$, these can be obtained from the corresponding alcohols (X=O) in various ways. For example, the corresponding alcohol is reacted with a sulfonyl chloride, for example toluenesulfonyl chloride, and the resulting sulfonic acid residue is then reacted with an azide. The corresponding azide of the particular azabicyclo[2.2.]heptane is obtained in this way. This azide can be reduced with conventional reducing agents, for example $LiAlH_4$, to the corresponding primary amine, resulting in a compound (IV) with X=NH.

The primary amine can also be obtained directly from said alcohol in a complex reaction. In this, the alcohol is reacted with hydrazoic acid $HN_3$ and an azodicarboxylate in the presence of a suitable phosphine, for example triphenylphosphine.

The primary amine can also converted into the secondary amine having a substituent $R^4$, for example by acylation and reduction of the carbonyl function, resulting in the required compound (IV) with $X=NR^4$.

The compounds of the formula (I) have at least one asymmetric carbon atom which may have different configurations. They can therefore exist in various optically active forms or else as racemates or mixture of racemates.

A base of the formula (I) can be converted with an acid into the relevant acid addition salt. Suitable and preferred for this reaction are acids which provide physiologically acceptable salts. Thus, it is possible to use inorganic acids, for example sulfuric acid, hydrovalic acids such as hydrochloric acid or hydrobromic acid, phosphoric acids such as orthophosphoric acid, nitric acid, sulfamic acid. Organic acids are likewise suitable, for example aliphatic, alicyclic, araliphatic, aromatic or heterocyclic mono-basic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- and ethanesulfonic acids, benzenesulfonic acid, p-toluenesulfonic acid, naphthalene mono- and disulfonic acids, lauryl sulfuric acid. Acid addition salts which are not physiologically acceptable (picrates) may be suitable for isolating and purifying the bases of the formula (I).

A base of the formula (I) can with some compounds (for example in the case of X=NH) be liberated from one of its salts with strong bases such as sodium or potassium hydroxide, sodium or potassium carbonate.

The compounds (I) set forth above are used to produce pharmaceuticals with which stimulation of the nicotinic acetylcholine receptors beneficially alters the pathological state.

These nicotinic acetylcholine receptors can in principle be divided into two main classes depending on the locations where they occur.

These are, on the one hand, the neuromuscular receptors. These are further divided into $(\alpha_1\alpha_1\beta\in\delta)$ and $(\alpha_1\alpha_1\beta\gamma\delta)$ receptors. On the other hand there are the neuronal nicotinic acetylcholine receptors which are found in the ganglia. With these, a distinction is made between the $(\beta_2-\beta_5)$ receptors and the $(\alpha_2-\alpha_9)$ receptors, in this connection also see "Basic Neurochemistry", Ed. Siegel et al., Raven Press, New York 1993.

The substances of the formula (I) are able, more or less well, depending, for example, on the structure of the particular molecule employed, to enter into an interaction with each of these receptors. The substances of the formula (I), especially those described as preferred hereinafter, interact particularly well with the nicotinic $\alpha_7$ receptor.

The in-vitro detection of the interaction with the nicotinic $\alpha_7$-receptor can be carried out analogously to J. M. Ward et al., FEBS 1990, 270, 45–48 or D. R. E. Macallan, FEB 1998, 226, 357–363. Further in-vitro tests for nicotinic receptors are described in F. E. D'Amour et al., Manual for Laboratory Work in Mammalian Physiology, $3^{rd}$ Ed., The University of Chicago Press (1965), W. Sihver et al., Neuroscience 1998, 85, 1121–1133 or B. Latli et al., J. Med. Chem. 1999, 42, 2227–2234.

Diseases which can be treated with the substances of the formula (I) comprise schizophrenia, dementia, in particular Alzheimer's disease, neurodegenerative disorders, Parkinson's disease, Tourette's syndrome, age-related memory weakness, alleviation of withdrawal symptoms, also, owing to the neuroprotective action, use for stroke and damage to the brain from toxic compounds.

The present invention further relates to pharmaceutical preparations comprising one or more compounds of the formula (I) and/or their physiologically active salts. For this purpose, they can be converted into a suitable dosage form together with at least one carrier or excipient and, where appropriate, in combination with one or more other active substances. These preparations can be employed as pharmaceuticals in human and veterinary medicine. Suitable carrier substances are organic or inorganic substances which are suitable for enteral (for example oral), parenteral or topical administration and which do not react with the novel compounds. Examples comprise water, vegetable oils, benzyl alcohols, polyethylene glycols, gelatin, carbohydrates such as lactose or starch, magnesium stearate, talc and petrolatum. Tablets, coated tablets, capsules, syrups, suspensions, drops or suppositories are used in particular for enteral administration, solutions, preferably oily or aqueous solutions, also suspensions, emulsions or implants, are used for parenteral administration, and ointments, creams, plasters or powders are used for topical applications. The novel compounds can also be lyophilized and the resulting lyophilizates can be used, for example, to produce products for injection.

The indicated preparations can be sterilized and/or contain excipients such as lubricants, preservatives, stabilizers and/or wetting agents, emulsifiers, salts to influence the osmotic pressure, buffer substances, colorings, flavorings and/or odorants. They may, if appropriate, also contain one or more other active substances which do not correspond to formula (I), for example one or more vitamins.

The substances of the invention are generally administered in analogy to known, commercially available products (for example tacrine), preferably in dosages between about 5 mg and 100 mg, in particular between 10 and 40 mg per dose unit. The daily dose is preferably between about 0.5 and 1 mg/kg of body weight.

The specific dose for each individual patient depends on a wide variety of factors, for example, on the efficacy of the specific compound employed, on the age, body weight, general state of health, sex, on the diet, on the time and route of administration, on the excretion rate, medicinal substance combination and severity of the particular disorder to which the therapy is applied.

Oral use is preferred.

The invention will now be illustrated in the following examples:

EXAMPLES

Example 1

200.00 mg (0.920 mmol) of (2-benzyl-2-aza-bicyclo[2.2.1]hept-7yl)methanol were dissolved in 3 ml of dry THF and then 176.00 mg (0.920 mmol) of ethyl 3-isocyanato-benzoate in 1 ml of dry THF were added at room temperature. After stirring for 6 hours at room temperature, 125 mg (0.30 mmol) of tris-(2-aminoethyl)amine-polystyrene and 250 mg (0.30 mmol) of methyl isocyanate-polystyrene (each from NovaBiochem) were added and stirred at 50° C. overnight. After the resins had been filtered off, the solvent was removed and the required product was purified by chromatography with ethyl acetate as mobile phase. In this way, 220.00 mg (0.539 mmol) of ethyl 3-(2-benzyl-2-azabicyclo[2.2.1]hept-7-ylmethoxycarbonylamino)benzoate were obtained in the form of a colorless solid.

150.00 mg (0.367 mmol) of this compound were then taken up in 2 ml of methanol and, after addition of 10.00 mg of palladium on activated carbon, stirred under a hydrogen atmosphere for 18 hours. Removal of the catalyst by filtration and removal of the solvent resulted in a colorless residue (103.00 mg, 0.324 mmol) containing ethyl 3-(2-azabicyclo[2.2.1]hept-7-ylmethoxycarbonylamino)benzoate.

15.919 mg (0.050 mmol) of this compound were dissolved in 0.5 ml of THF, then 10.119 mg (0.10 mmol) of triethylamine were added, and subsequently 6.125 mg (0.060 mmol) of acetic anhydride were added drop-wise. The solution was stirred at room temperature for 18 hours and quenched with water, and the organic phase after addition of ethyl acetate (2 ml) was isolated. Removal of the solvent and drying resulted in 18.00 mg of crude ethyl 3-(2-acetyl-2-aza-bicyclo[2.2.1]hept-7-yl-methoxycarbonylamino)benzoate in the form of a colorless oil, which can be further purified by conventional methods. $M^+$ (EI): 361

The following were obtained analogously:

2-Benzyl-2-azabicyclo[2.2.1]hept-7-ylmethyl (2,6-dichlorophenyl)-carbamate; $M^+$ (EI): 406

2-Benzyl-2-azabicyclo[2.2.1]hept-7-ylmethyl (4-phenoxyphenyl)carbamate; $M^+$ (EI): 430

2-Benzyl-2-azabicyclo[2.2.1]hept-7-ylmethyl (2-nitrophenyl)carbamate; $M^+$ (EI): 382

Ethyl 3-(2-benzyl-2-azabicyclo[2.2.1]hept-7-ylmethoxycarbonylamino)-benzoate; $M^+$ (EI): 409

2-Azabicyclo[2.2.1]hept-7-ylmethyl (3,4-dichlorophenyl) carbamate; $M^+$ (EI): 316

2-Azabicyclo[2.2.1]hept-7-ylmethyl (3,5-bistrifluoromethylphenyl)carbamate; $M^+$ (EI): 383

2-Azabicyclo[2.2.1]hept-7-ylmethyl (2,4-dimethoxyphenyl) carbamate; $M^+$ (EI): 307

Ethyl 3-(2-azabicyclo[2.2.1]hept-7-ylmethoxycarbonylamino)benzoate; $M^+$ (EI): 319

2-Benzyl-2-azabicyclo[2.2.1]hept-7-ylmethyl (4-fluoro-3-nitrophenyl)carbamate; $M^+$ (EI): 400

2-Benzyl-2-azabicyclo[2.2.1]hept-7-ylmethyl (3,5-bistrifluoromethyl-phenyl)carbamate; $M^+$ (EI): 473

2-Benzyl-2-azabicyclo[2.2.1]hept-7-ylmethyl (3,4,5-trimethoxyphenyl)carbamate; $M^+$ (EI): 428

2-Benzyl-2-azabicyclo[2.2.1]hept-7-ylmethyl (3,4-dichlorophenyl)carbamate; $M^+$ (EI): 406

Ethyl 3-[2-(4-trifluoromethylphenylcarbamoyl)-2-azabicyclo[2.2.1]hept-7-ylmethoxycarbonylamino]benzoate; $M^+$ (EI): 506

Ethyl 3-[2-(toluene-4-sulfonyl)-2-azabicyclo[2.2.1]hept-7-ylmethoxycarbdnylamino]benzoate; $M^+$ (EI): 474

Ethyl 3-(2-ethoxycarbonylmethyl-2-azabicyclo[2.2.1]hept-7-yl-methoxycarbonylamino)benzoate; $M^+$ (EI): 405

2-Benzyl-2-azabicyclo[2.2.1]hept-7-ylmethyl(3-cyanophenyl)carbamate; $M^+$ (EI): 362

2-Benzyl-2-azabicyclo[2.2.1]hept-7-ylmethyl (2,6-dichloropyridin-4-yl)carbamate; $M^+$ (EI): 407

2-Benzyl-2-azabicyclo[2.2.1]hept-7-ylmethyl (3-acetylphenyl)carbamate; $M^+$ (EI): 379

1-(2-Benzyl-2-azabicyclo[2.2.1]hept-7-ylmethyl)-3-(3,4,5-trimethoxyphenyl)urea; $M^+$ (EI): 427

1-(2-Benzyl-2-azabicyclo[2.2.1]hept-7-ylmethyl)-3-(2-nitrophenyl)urea; $M^+$ (EI): 381.

Example 2

1) 0.5 g of (2-benzyl-2-azabicyclo[2.2.1]hept-7-yl)methanol in 2 ml of dried pyridine was added at 0° C. to an efficiently stirred solution of 0.6 g of tosyl chloride in 5 ml of dried pyridine. The mixture was stirred at 0° C. for 12 h, poured into ice and stirred for a further hour. The resulting oil was extracted with ethyl acetate, and the organic phase was washed twice with water, then dried and evaporated to dryness. The resulting (2-benzyl-2-azabicyclo[2.2:1]hept-7-ylmethyl)-toluene4-sulfonate was employed without further purification in stage 2). Yield: 99.3% of theory ESI-MS: 372

2) The product obtained in step 1) (0.583 g) was dissolved in 3 ml of dimethylformamide and added at room temperature to a suspension of $NaN_3$ (0.715 g) in 10 ml of dimethylformamide. After the addition was complete, the mixture was stirred at 85° for 18 h, poured into ice-water and extracted with ethyl acetate. The organic phase was dried and concentrated under reduced pressure to a colorless oil which comprised pure 7-azidomethyl-2-benzyl-2-azabicyclo[2.2. 1]heptane.

Yield: 84.1% of theory ESI-MS: 243

3) A solution of the product obtained in step 2) (0.320 g) in 5 ml of THF was added dropwise to a suspension of 0.114 g of LiAlH$_4$ in 10 ml of THF. After the addition was complete, the mixture was stirred at room temperature overnight. A 2N NaOH solution was added and the mixture was filtered and washed with ethyl acetate, the organic phase was separated off, and the aqueous phase was re-extracted with ethyl acetate. The combined organic phases were dried and the solvent was removed. Part of the resulting (2-benzyl-2-azabicyclo[2.2. 1 .]hept-7-yl)methylamine was converted into the corresponding dihydrochloride.

Yield: 80.5% of theory ESI-MS: 217

Example 3

A 0.4M solution of 0.108 g of hydrazoic acid in 6.25 ml of toluene was added to a solution of (2-benzyl-2-azabicyclo[2.2.1]hept-7-yl)methanol (217 mg) in 1 ml of anhydrous THF. Then a solution of 0.461 g of diisopropyl azodicarboxylate in 1.5 ml of THF and a solution of 1.31 g of triphenylphosphine in 2 ml THF were added. The temperature of this solution was kept at 25° C. by addition of this latter solution in doses. The solution was stirred at temperatures between 25 and 50° C. for a total of 19 h, then 0.5 ml of water was added, the mixture was stirred at 50° C. for a further 6 h, the solvent was removed in vacuo, and the resulting residue was mixed with 10 ml of methylene chloride and 10 ml of 1N HCl. The aqueous phase was removed and washed repeatedly with methylene chloride. Removal of the water under reduced pressure resulting in (2-benzyl-2-azabicyclo[2.2.1]hept-7-yl)methylamine in the form of a colorless oil.

Yield: 52% of theory

Example 4

The amine obtained in examples 2 and 3 (30 mg) was dissolved in 1 ml of THF and, at room temperature, 28.131 mg of triethylamine were added and 17.355 mg of acetic anhydride were added dropwise. The solution was stirred at room temperature for 18 h and quenched with water, and the organic phase after addition of ethyl acetate was isolated. Drying and removal of the solvent resulted in (2-benzyl-2-azabicyclo[2.2. 1]hept-7-ylmethyl)acetamide.

Yield: 89% of theory ESI-MS: 259

Example 5

3.795 mg of LiAlH$_4$ were introduced into 1 ml of THF, and 20 mg of the amide obtained in example 4, which were dissolved in 1 ml of THF, were added dropwise. The mixture was stirred at 0° C. for 1 h and then at room temperature. Water was then added to the mixture, followed by an aqueous NH$_3$ solution, and the mixture was filtered and extracted with ethyl acetate. The organic phase was dried and the solvent was evaporated. 18 mg of (2-benzyl-2-azabicyclo[2.2.1]hept-7-ylmethyl)ethylamine were, obtained in this way.

Yield: 96% of theory ESI-MS: 245

(2-Benzyl-2-azabicyclo[2.2.1]hept-7-yl)methanediol has likewise been prepared, ESI-MS: 234

The following examples relate to pharmaceutical preparations containing substances of the formula (I) or one of their acid addition salts:

Example A

Tablets

A mixture of 1 kg of ethyl 3-(2-acetyl-2-azabicyclo[2.2.1]hept-7-ylmethoxycarbonylamino)benzoate, 4 kg of lactose, 1.2 kg of potato starch, 0.2 kg of talc and 0.1 kg of magnesium stearate is compressed to tablets in a conventional way so that each tablet contains 10 mg of active substance.

Example B

Coated Tablets

Tablets are compresssed in analogy to example A and are then provided in a conventional way with a coating of sucrose, potato starch, talc, tragacanth and coloring.

Example C

Capsules 2 kg of ethyl 3-(2-acetyl-2-azabicyclo[2.2.1]hept-7-yl-methoxycarbonylamino)benzoate are packed into hard gelatin capsules in a conventional way so that each capsule contains 20 mg of active substance.

Example D

Ampules

A solution of 1 kg of ethyl 3-(2-acetyl-2-azabicyclo[2.2.1]hept-7-yl-methoxycarbonylamino)benzoate [lacuna] in 60 l of double-distilled water is sterilized by filtration, dispensed into ampules, lyophilized under sterile conditions and sealed sterile. Each ampule contains 10 mg of active substance.

Tablets, coated tablets, capsules and ampules containing another compound of the formula (I) and/or one or more physiologically acceptable acid addition salts of a compound of the formula (I) can be obtained analogously.

The invention claimed is:

1. A compound of formula

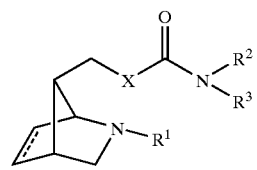

I in which
the broken line represents a double bond which is optionally present,
X is NH, NR$^4$, O or S,
R$^1$ is hydrogen, a linear or branched, substituted or unsubstituted C$_1$–C$_{10}$-alkyl group, substituted or unsubstituted C$_5$–C$_{10}$-aryl group, substituted or unsubstituted C$_4$–C$_{10}$-heteroaryl group, acyl group, thioacyl group, carbonylcarboxy group, N-organyl-substituted carbamoyl group or organosulfonyl group,
R$^2$, R$^3$ and $R^4$ are, independently of one another, a $C_1$–$C_{10}$-alkyl group, $C_5$–$C_{12}$-aryl group or $C_4$–$C_{12}$-heteroaryl group, these groups being unsubstituted or having one or more substituents which are, independently of one another, a halogen, alkoxy group, aryloxy group, nitro group, $C_1$–$C_5$-alkoxycarbonyl group, optionally fluorine-substituted alkyl or acyl group or cyano group, or a physiologically acceptable salt thereof.

2. A compound according to claim 1, in which

X is NH, $NR^4$ or O, $R^1$ is a hydrogen, a linear or branched $C_1$–$C_5$-alkyl group which is unsubstituted or optionally substituted with one or more halogen atoms, optionally alkyl-substituted $C_6$–$C_{10}$-aryl groups, $C_1$–$C_5$-alkoxycarbonyl groups, $C_6$–$C_{12}$-aryl groups or $C_5$–$C_{10}$-heteroaryl groups which may be unsubstituted or have as substituents in each case one or more halogen atoms and/or alkyl groups, or aliphatic $C_1$–$C_5$-acyl or thioacyl groups, aromatic $C_6$–$C_9$-aroyl or thioaroyl groups, carbamoyl groups of the type $R^5$—N(H)—C(O)— or sulfonyl groups of the type $R^5$—$SO_2$—, $R^2$, $R^3$ and $R^4$ are, independently of one another, a $C_1$–$C_4$-alkyl group, $C_5$–$C_8$-aryl group or $C_5$–$C_8$-heteroaryl group which is unsubstituted or have one or more substituents which are, each independently, a $C_1$–$C_3$-alkoxy group, $C_6$–$C_9$-aryloxy group, nitro group, $C_1$–$C_2$-alkoxycarbonyl group, cyano group, fluoride, chloride, fluoromethyl group or acetyl group, $R^3$ is a $C_1$–$C_3$-alkyl group, $C_1$–$C_3$-fluoroalkyl group or phenyl group which can be unsubstituted or substituted by one or more methyl or trifluoromethyl groups, or a physiologically acceptable salt thereof.

3. A compound which is
2-Benzyl-2-azabicyclo[2.2.1]hept-7-ylmethyl(2,6-dichlorophenyl)carbamate,
2-Benzyl-2-azabicyclo[2.2.1]hept-7-ylmethyl(4-phenoxyphenyl)carbamate,
2-Benzyl-2-azabicyclo[2.2.1]hept-7-ylmethyl(2-nitrophenyl)carbamate,
Ethyl 3-(2-benzyl-2-azabicyclo[2.2.1]hept-7-ylmethoxycarbonylamino)benzoate,
2-Azabicyclo[2.2.1]hept-7-ylmethyl(3,4-dichlorophenyl)carbamate,
2-Azabicyclo[2.2.1]hept-7-ylmethyl(3,5-bistrifluoromethylphenyl)carbamate,
2-Azabicyclo[2.2.1]hept-7-ylmethyl(2,4-dimethoxyphenyl)carbamate,
Ethyl 3-(2-azabicyclo[22.1]hept-7-ylmethoxycarbonylamino)benzoate,
2-Benzyl-2-azabicyclo[22.1]hept-7-ylmethyl(4-fluoro-3-nitrophenyl)carbamate,
2-Benzyl-2-azabicyclo[2.2.1]hept-7-ylmethyl(3,5-bistrifluoromethylphenyl)carbamate,
2-Benzyl-2-azabicyclo[2.2.1]hept-7-ylmethyl(3,4,5-trimethoxyphenyl)carbamate,
2-Benzyl-2-azabicyclo[2.2.1]hept-7-ylmethyl(3,4-dichlorophenyl)carbamate,
Ethyl 3-[2-(4-trifluoromethylphenylcarbamoyl)-2-azabicyclo[2.2.1]hept-7-ylmethoxycarbonylamino]benzoate,
Ethyl 3-[2-(toluene-4-sulfonyl)-2-azabicyclo[2.2.1]hept-7-ylmethoxycarbonylamino]benzoate,
Ethyl 3-(2-ethoxycarbonylmethyl-2-azabicyclo[2.2.1]hept-7-yl-methoxycarbonylamino)benzoate,
2-Benzyl-2-azabicyclo[2.2.1]hept-7-ylmethyl(3-cyanophenyl)carbamate,
2-Benzyl-2-azabicyclo[2.2.1]hept-7-ylmethyl(2,6-dichloropyridin-4-yl)carbamate,
2-Benzyl-2-azabicyclo[2.2.1]hept-7-ylmethyl(3-acetylphenyl)carbamate,
1-(2-Benzyl-2-aza-bicyclo[2.2.1]hept-7-ylmethyl)-3-(3,4,5-trimethoxy-phenyl)urea, or
1-(2-Benzyl-2-aza-bicyclo[2.2.1]hept-7-ylmethyl)-3-(2-nitrophenyl)urea, or a physiologically acceptable salt thereof.

4. A compound of formula III

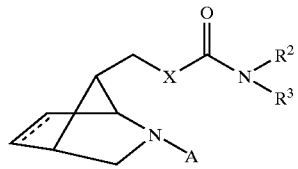

in which the broken line represents a double bond which is optionally present,

X is NH, $NR^4$, O or S, $R^2$, $R^3$ and $R^4$ are, independently of one another, a $C_1$–$C_{10}$-alkyl group, $C_5$–$C_{12}$-aryl group or $C_4$–$C_{12}$-heteroaryl group, these groups being unsubstituted or having one or more substituents which are independently of one another, a halogen alkoxy group, aryloxy group, nitro group, $C_1$–$C_5$-alkoxycarbonyl group, optionally fluorine-substituted alkyl or acyl group or cyano group, and A is hydrogen or a protective group.

5. A pharmaceutical composition comprising a compound as claimed in claim 1 or a physiologically acceptable salt thereof and an excipient.

6. A compound according to claim 2, in which X is O.

* * * * *

UNITED STATES PATENT AND TRADEMARK OFFICE
CERTIFICATE OF CORRECTION

PATENT NO. : 7,008,955 B2 Page 1 of 1
APPLICATION NO. : 10/380064
DATED : March 7, 2006
INVENTOR(S) : Kai Schiemann et al.

It is certified that error appears in the above-identified patent and that said Letters Patent is hereby corrected as shown below:

Column 9, line 24, reads "$C_5$-$C_8$-aryl" should read -- $C_5$-$C_9$-aryl --
Column 9, line 26, reads "$C_1$-$C_3$-alkoxy" should read -- $C_1$-$C_4$-alkoxy --
Column 9, line 30, reads "$R^3$" should read -- $R^5$ --
Column 9, line 49, reads "[22.1]" should read -- [2.2.1] --
Column 9, line 51, reads "[22.1]" should read -- [2.2.1] --
Column 10, line 44, reads "are independently" should read -- are, independently --
Column 10, line 45, reads "halogen alkoxy" should read -- halogen, alkoxy --

Signed and Sealed this

Nineteenth Day of September, 2006

JON W. DUDAS
*Director of the United States Patent and Trademark Office*